United States Patent
Caillon-Morisseau et al.

(10) Patent No.: US 8,536,211 B2
(45) Date of Patent: Sep. 17, 2013

(54) PROCESS FOR THE PREPARATION OF 5-SUBSTITUTED 1-ALKYLTETRAZOLES

(75) Inventors: Stéphane Caillon-Morisseau, Lyons (FR); Pierre-Yves Coqueron, Lyons (FR); Jens-Dietmar Heinrich, Burscheid (DE); Robert Lui, Odenthal (DE)

(73) Assignee: Bayer Intellectual Property GmbH (DE)

( * ) Notice: Subject to any disclaimer, the term of this patent is extended or adjusted under 35 U.S.C. 154(b) by 0 days.

(21) Appl. No.: 13/582,026

(22) PCT Filed: Mar. 11, 2011

(86) PCT No.: PCT/EP2011/053660
§ 371 (c)(1),
(2), (4) Date: Aug. 30, 2012

(87) PCT Pub. No.: WO2011/110651
PCT Pub. Date: Sep. 15, 2011

(65) Prior Publication Data
US 2012/0330027 A1    Dec. 27, 2012

Related U.S. Application Data

(60) Provisional application No. 61/313,859, filed on Mar. 15, 2010.

(30) Foreign Application Priority Data

Mar. 12, 2010  (EP) ..................................... 10156377

(51) Int. Cl.
*A61K 31/41* (2006.01)
*C07D 257/04* (2006.01)

(52) U.S. Cl.
USPC ........................................... 514/381; 548/250

(58) Field of Classification Search
USPC .......................... 514/381, 383; 548/250, 255
See application file for complete search history.

(56) References Cited

FOREIGN PATENT DOCUMENTS

| WO | PCT/EP2009/058427 | | 7/2009 |
|---|---|---|---|
| WO | 2010/000841 | | 1/2010 |
| WO | WO 2010/103783 | * | 9/2010 |

OTHER PUBLICATIONS

Yates, et al., JACS, vol. 85(19), 1963, pp. 2967-2976.*
International Search Report issued Apr. 18, 2011 in International Application No. PCT/EP2011/053660.
Peter Yates and Donald G. Farnum: "Aliphatic Diazo Compounds. The Reaction of Diazo Ketones with Bases", J. Amer.Chem. Soc., vol. 85, No. 19, pp. 2967-2976, Oct. 1963, XP-002580503.
Ivar Ugi and Uwe Fetzer: "Isonitrile. Die Addition von Carbonsaurechloriden an Isonitrile", Chem. Ber., vol. 94, No. 4, Apr. 1, 1961, XP-002580502 and English language translation thereof.

* cited by examiner

*Primary Examiner* — Susannah Chung
(74) *Attorney, Agent, or Firm* — Ostrolenk Faber LLP

(57) ABSTRACT

The present invention relates to a process for the preparation of 5-substituted 1-alkyltetrazoles.

8 Claims, No Drawings

PROCESS FOR THE PREPARATION OF 5-SUBSTITUTED 1-ALKYLTETRAZOLES

CROSS-REFERENCE TO RELATED APPLICATION(S)

The present application is a 35 U.S.C. §371 national phase conversion of PCT/EP2011/053660 filed Mar. 11, 2011 which claims priority of European Application No. 10156377.3 filed Mar. 12, 2010 and U.S. Provisional Application Ser. No. 61/313,859 filed Mar. 15, 2010. Applicants claim priority to each of the foregoing patent applications. The PCT International Application was published in the English language.

The present invention relates to a process for the preparation of 5-substituted 1-alkyltetrazoles.

5-substituted 1-alkyltetrazoles are important intermediate compounds in active ingredient manufacture (see e.g. WO 2010/000841).

It is already known that 5-substituted 1-alkyltetrazoles can be prepared by lithiation of 1-methyltetrazole at −70° C. (cf. Can. J. Chem. 1971, 49, 2139-2142). However, the yield using the example of 5-benzoyl-1-methyltetrazole is only 41%. The 1-methyltetrazole used likewise has to be prepared in a multistage synthesis sequence. For an industrial reaction, the low temperatures and the expensive use of butyllithium are disadvantageous.

Another process for the preparation of 5-benzoyl-1-methyltetrazole is known from J. Amer. Chem. Soc. 1963, 85, 2967-2976. Benzyl cyanide is reacted with ammonium azide to give 5-benzyltetrazole and then oxidized with chromium trioxide to give 5-benzoyltetrazole. The methylation to 5-benzoyl-1-methyltetrazole takes place with diazomethane. This synthesis route is likewise disadvantageous as regards safety and economical aspects.

The preparation of 1-cyclohexyl-5-acetyltetrazole by reacting acetyl chloride over cyclohexyl isocyanide with subsequent reaction with hydrazoic acid is also known (cf. Chem. Ber. 1961, 94, 1116-1121). Hydrazoic acid is an unstable, extremely explosive and very toxic liquid which cannot be used on an industrial scale.

Starting from the known processes for the preparation of 5-substituted 1-alkyltetrazoles, the object now is how these can be prepared safely and cost-effectively, so that the process can also be used for the industrial production of 5-substituted 1-alkyltetrazoles.

A process to give 5-substituted 1-alkyltetrazoles has now been found which overcomes the aforementioned disadvantages.

The invention therefore provides a process for the preparation of 5-substituted 1-alkyltetrazoles of the formula (I)

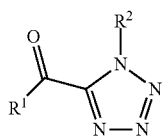

(I)

in which $R^1$ is alkyl, or phenyl optionally monosubstituted by halogen, cyano, nitro, $C_1$-$C_8$-alkyl, $C_1$-$C_8$-alkoxy, methylsulphonyl, trifluoromethyl or aryl, $R^2$ is $C_1$-$C_{12}$-alkyl, $C_1$-$C_{12}$-haloalkyl or an alkoxyalkyl of the formula -[A-O]$_m$—B, A is $C_2$-$C_4$-alkanediyl (alkylene), B is $C_1$-$C_6$-alkyl, m is 1 or 2, characterized in that (1) in a first step, an acid chloride of the formula (II)

(II)

in which $R^1$ has the meanings given above and X is halogen, is reacted with an alkyl isocyanide of the formula (III)

(III)

in which $R^2$ has the meanings given above, and the imines of the formula (IV) obtained in this way

(IV)

in which $R^1$, $R^2$ and X have the meanings given above, (2) are reacted in a second step with azides of the formula (V)

in which $R^3$ is sodium, potassium, tetrabutylammonium, trimethylsilyl, diphenylphosphoryl, optionally in the presence of a base.

The process according to the invention can be illustrated by reference to the following scheme:

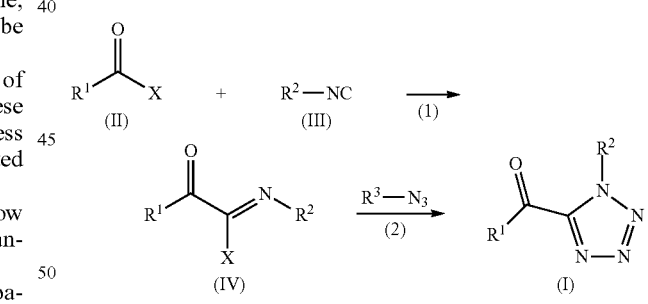

The acid chlorides used as starting materials when carrying out the process according to the invention are generally defined by the formula (II).

$R^1$ is preferably $C_1$-$C_8$-alkyl, or phenyl optionally monosubstituted by fluorine, chlorine, bromine, iodine, cyano, nitro, $C_1$-$C_6$-alkyl, methylsulphonyl, trifluoromethyl or phenyl or naphthyl.

$R^1$ is particularly preferably $C_1$-$C_6$-alkyl, or phenyl optionally monosubstituted by fluorine, chlorine, $C_1$-$C_4$-alkyl or $C_1$-$C_3$-alkoxy, $R^1$ is very particularly preferably methyl, ethyl, n-propyl, isopropyl, n-, i-, s- or t-butyl, or phenyl optionally monosubstituted by fluorine, chlorine, methyl, t-butyl, methoxy or ethoxy, $R^1$ is especially preferably unsubstituted phenyl.

X is preferably fluorine, chlorine or bromine
X is particularly preferably fluorine or chlorine.
X is very particularly preferably chlorine.

Acid chlorides of the formula (II) are known, e.g. commercially available, or can be prepared by known processes.

The alkyl isocyanides further used as starting materials for carrying out the process according to the invention are generally defined by the formula (III).

$R^2$ is preferably $C_1$-$C_8$-alkyl, $C_1$-$C_8$-haloalkyl or an alkoxyalkyl of the formula -[A-O]$_m$—B.
$R^2$ is particularly preferably $C_1$-$C_4$-alkyl, $C_1$-$C_4$-haloalkyl or an alkoxyalkyl of the formula -[A-O]$_m$—B.
$R^2$ is very particularly preferably methyl, ethyl, trifluoromethyl, or an alkoxyalkyl of the formula -[A-O]$_m$—B.
$R^2$ is especially preferably methyl.
A is preferably —$(CH_2)_2$—, —$(CH_2)_3$—, —$CH(CH_3)$— or —$CH(CH_3)CH_2$—.
A is particularly preferably —$(CH_2)_2$— or —$CH(CH_3)CH_2$—.
A is very particularly preferably —$(CH_2)_2$—.
B is preferably $C_1$-$C_6$-alkyl.
B is particularly preferably $C_1$-$C_4$-alkyl.
B is very particularly preferably methyl or ethyl.
m is preferably 1.

Alkyl isocyanides of the formula (III) are known, e.g. commercially available, or can be prepared by known processes (cf. *Angew. Chem. Int. Ed.* 1965, 4, 472-484).

The azides further used as starting materials when carrying out the process according to the invention are generally defined by the formula (V).

$R^3$ is preferably sodium or trimethylsilyl.
$R^3$ is particularly preferably sodium.

Azides of the formula (V) are known, e.g. commercially available, or can be prepared by known processes.

The term "alkyl"—on its own or in combination with other terms, such as, for example, arylalkyl or alkoxy—refers to linear or branched saturated hydrocarbon chains having up to 12 carbon atoms, i.e. $C_1$-$C_{12}$-alkyl, preferably with up to 6 carbon atoms, i.e. $C_1$-$C_6$-alkyl, particularly preferably having up to 4 carbon atoms, i.e. $C_1$-$C_4$-alkyl. Examples of such alkyls are methyl, ethyl, n-propyl or isopropyl, n-, i-, s- or t-butyl, n-pentyl, n-hexyl, n-heptyl, n-octyl, n-nonyl, n-decyl, n-undecyl and n-dodecyl. The alkyls can be substituted with a suitable substituent, e.g. with halogen.

The term "aryl"—on its own or in combination with other terms—refers to cyclic aromatic non-condensed or condensed groups which have 5 to 18 carbon atoms. Preferred aryls have 6 to 14 carbon atoms (e.g. phenyl or naphthyl). Among the aryls, phenyl is particularly preferred.

"Halogen" or "Hal" stands for fluorine, chlorine, bromine or iodine.

The second reaction step (2) is optionally carried out in the presence of a base. However, this step can also be carried out without base, although the reaction rate is faster with base. It is described in the literature (cf. *Chem. Ber.* 1961, 94, 1116-1121) that the α-keto carboxylic acid imide chlorides cleave with strong bases such as alkali metal hydroxides, ammonia and also amines with elimination. Surprisingly, the addition of base in the process according to the invention is advantageous. The reaction preferably takes place in the presence of a base. Suitable bases are organic and inorganic bases which are usually used in such reactions. Preference is given to using bases which are selected for example from the group of tertiary amines, such as trimethylamine, triethylamine, tributylamine, N,N-dimethylaniline, N,N-dimethylbenzylamine, pyridine, alkylpyridines, such as 2,6-dimethylpyridine, 2-methyl-5-ethylpyridine, N-methylpiperidine, N-methylpyrolidone, N,N-dimethylaminopyridine, diazabicyclooctane (DABCO), diazabicyclononene (DBN) and diazabicycloundecene (DBU).

The imines of the formula (IV) obtained in step (1) can either be isolated or be further reacted directly in situ. Preferably, the imines of the formula (IV) are further reacted in situ.

In step (1), it is preferred according to the invention to introduce the acid chloride of the formula (II) as initial charge either without solvent, i.e. without dilution, or in a suitable solvent, and then to add the alkylisocyanide of the formula (III), which is optionally dissolved in a suitable solvent. It is also possible to introduce the alkyl isocyanide as initial charge and to meter in the acid chloride. A parallel metered addition of the two components is also possible.

In step (2), the reaction is preferably carried out in a solvent. The solvents are preferably used in an amount such that the reaction mixture remains readily stirrable throughout the entire process. Suitable solvents for carrying out the process according to the invention are all organic solvents inert under the reaction conditions. According to the invention, solvents are also understood as meaning mixtures of pure solvents.

Solvents suitable according to the invention are in particular ethers (e.g. ethyl propyl ether, methyl tert-butyl ether, n-butyl ether, anisole, phenetol, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; aliphatic, cycloaliphatic or aromatic hydrocarbons (e.g. pentane, hexane, heptane, octane, nonane, such as the so-called "white spirits" with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, xylene); halogenated hydrocarbons, such as chlorobenzene, dichlorobenzene, dichloromethane, chloroform, tetrachloromethane, dichloroethane or trichloroethane; esters (e.g. methyl, ethyl, butyl, isobutyl acetate, dimethyl, dibutyl or ethylene carbonate, propylene carbonate); amides (e.g. hexamethylene phosphortriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine); nitriles, such as acetonitrile, propionitrile, n- or isobutyronitrile or benzonitrile; ketones such as acetone or mixtures thereof.

For the reaction according to the invention, the solvents used are preferably aromatic and/or aliphatic hydrocarbons, nitriles, ethers, in particular toluene, acetonitrile, THF, methylene chloride.

The process according to the invention can generally be carried out in vacuo, at atmospheric pressure or under superatmospheric pressure.

The temperatures used can vary depending on the starting materials. The process according to the invention in step (1)

can be carried out at temperatures in the range from 20° C. to 150° C., preferably at an internal temperature in the range from 30° C. to 120° C., in particular in the range from 40° C. to 110° C. The process according to the invention in step (2) takes place at temperatures from −20 to +80° C., preferably at temperatures from −10 to +70° C.

The ratio of the acid halide of the formula (II) used to the alkyl isocyanide of the formula (III) used can vary. Preferably, the ratio of acid chloride of the formula (II) to the alkyl isocyanide of the formula (III) used is in the range from 1:1 to 1:4, in particular in the range from 1:1 to 1:2, specifically from 1:1.1 to 1:1.4.

The ratio of imine of the formula (IV) to the azide of the formula (V) can vary. A significant excess is not critical for the reaction, but is uneconomic. Preferably, the ratio of imine of the formula (IV) to the azide of the formula (V) is in the range from 1:1 to 1:3, in particular in the range from 1:1 to 1:2, specifically in the range from 1:1.0 to 1:1.3. Since preferably the imines of the formula (IV) are not isolated, the required quantitative ratio is determined with regard to the amount of acid halide of the formula (II) used.

The present invention is illustrated in more detail by reference to the examples below, without thereby limiting the invention thereto.

PREPARATION EXAMPLES

Example 1

At room temperature, 10 g of benzoyl chloride (71 mmol) were admixed with 3.7 g (92 mmol) of methyl isocyanide. The mixture was then heated at 60° C. for 3 hours. The mixture was admixed with 25 ml of acetonitrile and cooled to 0° C. The reaction mixture was added to 4.6 g of sodium azide (71 mmol) in 9.1 g of 2,6-dimethylpyridine (85 mmol) in 25 ml of acetonitrile at 0° C. The mixture was then heated to 60° C. and stirred at this temperature for 1 hour. At room temperature, 100 ml of water and 100 ml of ethyl acetate were added to the mixture. The organic phase was separated off and the aqueous phase was extracted with 100 ml of ethyl acetate. The combined organic phases were dried over magnesium sulphate and the solvent was removed in vacuo. This gave 1-methyl-5-benzoyltetrazole in a yield of 82% (purity 90%) based on the acid chloride used. The crude product could be recrystallized from 20 ml of isopropanol, giving 9.4 g of 1-methyl-5-benzoyltetrazole (purity 97.4%).

$^1$H-NMR (DMSO, 298K) δ: 4.39 (s, 3H), 7.65 (t, 2H), 7.80 (t, 1H), 8.27 (d, 2H)

Example 2

At room temperature, 10 g of benzoyl chloride (71 mmol) were admixed with 3.7 g (92 mmol) of methyl isocyanide. The mixture was then heated at 60° C. for 2 hours. The mixture was admixed with 25 ml of acetonitrile and cooled to 0° C. This reaction mixture was added to 4.6 g of sodium azide (71 mmol) in 25 ml of acetonitrile at 0° C. The mixture was then heated to 60° C. to 65° C. and stirred at this temperature for 16 hours. At room temperature, 100 ml of water and 100 ml of ethyl acetate were added to the mixture. The organic phase was separated off and the aqueous phase was extracted with 100 ml of ethyl acetate. The combined organic phases were dried over magnesium sulphate and the solvent was removed in vacuo. The crude product could be recrystallized from 20 ml of isopropanol, giving 8.7 g of 1-methyl-5-benzoyltetrazole (purity 99.4%). This corresponds to a yield of 65%, based on the acid chloride used.

Example 3

At room temperature, 1 g of benzoyl chloride (7.1 mmol) was admixed with 0.38 g (9.2 mmol) of methyl isocyanide. The mixture was then heated at 60° C. for 3 hours. The mixture was admixed with 2.5 ml of acetonitrile and cooled to 0° C. This reaction mixture was added to 0.46 g of sodium azide (7.1 mmol) in 0.6 g of pyridine (8.5 mmol) in 2.5 ml of acetonitrile at 0° C. The mixture was then heated to 60° C. and stirred at this temperature for 1 hour. At room temperature, 10 ml of water and 10 ml of ethyl acetate were added to the mixture. The organic phase was separated off and the aqueous phase was extracted with 10 ml of ethyl acetate. The combined organic phases were dried over magnesium sulphate and the solvent was removed in vacuo. This gave 1-methyl-5-benzoyltetrazole in a yield of 70.5% (purity 89%), based on the acid chloride used.

Example 4

At room temperature, 10 g of benzoyl chloride (71 mmol) were admixed with 3.7 g (92 mmol) of methyl isocyanide. The mixture was then heated at 60° C. for 3 hours. The mixture was admixed with 25 ml of acetonitrile and cooled to 0° C. This reaction mixture was added to 4.6 g of sodium azide (71 mmol) in 1.1 g (14 mmol) of pyridine in 25 ml of acetonitrile at 0° C. The mixture was then heated to 60° C. and stirred at this temperature for 1 hour. At room temperature, 100 ml of water and 100 ml of ethyl acetate were added to the mixture. The organic phase was separated off and the aqueous phase was extracted with 100 ml of ethyl acetate. The combined organic phases were dried over magnesium sulphate and the solvent was removed in vacuo. The crude product was recrystallized from 20 ml of isopropanol, giving 8.83 g of 1-methyl-5-benzoyltetrazole (purity 99.6%).

The invention claimed is:
1. A process for the preparation of a 5-substituted 1-alkyltetrazole of the formula (I)

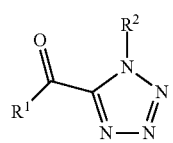

(I)

in which
R$^1$ is selected from the group consisting of
(A) alkyl and
(B) phenyl optionally monosubstituted by a member selected from the group consisting of halogen, cyano, nitro, $C_1$-$C_8$-alkyl, $C_1$-$C_8$-alkoxy, methylsulphonyl, trifluoromethyl and aryl,
R$^2$ is selected from the group consisting of $C_1$-$C_{12}$-alkyl, $C_1$-$C_{12}$-haloalkyl and an alkoxyalkyl of the formula -[A-O]$_m$—B,
wherein
A is $C_2$-$C_4$-alkanediyl (alkylene),
B is $C_1$-$C_6$-alkyl, and
m is 1 or 2, comprising the steps of:
(1) reacting an acid halide of the formula (II)

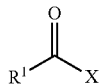  (II)

in which X is halogen,
with an alkyl isocyanide of the formula (III)

$R^2$—NC  (III)

to form an imine of the formula (IV)

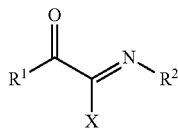  (IV)

(2) and then reacting the imine (IV) with an azide of the formula (V)

$R^3$—$N_3$  (V)

in which $R^3$ is selected from the group consisting of sodium, potassium, tetrabutylammonium, trimethylsilyl, and diphenylphosphoryl,
optionally in the presence of a base, to form the 5-substituted 1-alkyltetrazole of the formula (I).

2. The process of claim 1 wherein
$R^1$ is selected from the group consisting of
(A) $C_1$-$C_8$-alkyl and
(B) phenyl optionally monosubstituted by a member selected from the group consisting of fluorine, chlorine, bromine, iodine, cyano, nitro, $C_1$-$C_6$-alkyl, methylsulfonyl, trifluoromethyl, phenyl, and naphthyl,
X is selected from the group consisting of fluorine, chlorine, and bromine,
$R^2$ is selected from the group consisting of $C_1$-$C_8$-alkyl, $C_1$-$C_8$-haloalkyl, and an alkoxyalkyl of the formula -[A-O]$_m$—B,
wherein
A is selected from the group consisting of —(CH$_2$)$_2$—, —(CH$_2$)$_3$—, —CH(CH$_3$)—, and —CH(CH$_3$)CH$_2$—,
B is $C_1$-$C_6$-alkyl, and
m is 1.

3. The process of claim 1 wherein
$R^1$ is selected from the group consisting of
(A) $C_1$-$C_6$-alkyl and
(B) phenyl optionally monosubstituted by a member selected from the group consisting of fluorine, chlorine, $C_1$-$C_4$-alkyl, and $C_1$-$C_3$-alkoxy,
X is selected from the group consisting of fluorine and chlorine,
$R^2$ is selected from the group consisting of $C_1$-$C_4$-alkyl, $C_1$-$C_4$-haloalkyl, and an alkoxyalkyl of the formula -[A-O]$_m$—B,
wherein
A is selected from the group consisting of —(CH$_2$)$_2$— and —CH(CH$_3$)CH$_2$—,
B is $C_1$-$C_4$-alkyl, and
m is 1.

4. The process of claim 1 wherein $R^1$ is an unsubstituted phenyl, X is chlorine, and $R^2$ is methyl.

5. The process of claim 1 wherein step (2) is carried out in the presence of a base.

6. The process of claim 1 wherein the imines of the formula (IV) are not isolated and are further used in situ.

7. The process of claim 5 wherein the base is selected from the group consisting of tertiary amines, pyridine, alkylpyridines, N-methylpiperidine, N-methylpyrolidone, N,N-dimethylaminopyridine, diazabicyclooctane, diazabicyclononene, and diazabicycloundecene.

8. The process of claim 7 wherein the base is selected from the group consisting of trimethylamine, triethylamine, tributylamine, N,N-dimethylaniline, N,N-dimethylbenzylamine, pyridine, 2,6-dimethylpyridine, 2-methyl-5-ethylpyridine, N-methylpiperidine, N-methylpyrolidone, N,N-dimethylaminopyridine, diazabicyclooctane, diazabicyclononene, and diazabicycloundecene.

* * * * *